United States Patent [19]

Ryan et al.

[11] 3,943,126
[45] Mar. 9, 1976

[54] PROCESS FOR ACYLATING A 7-AMINOCEPHALOSPORIN

[75] Inventors: Charles W. Ryan; William B. Blanchard, both of Indianapolis, Ind.

[73] Assignee: Eli Lilly and Company, Indianapolis, Ind.

[22] Filed: Nov. 15, 1973

[21] Appl. No.: 416,296

[52] U.S. Cl............ 260/243 C; 424/246; 260/239.1
[51] Int. Cl.²...................................... C07D 501/06
[58] Field of Search ................................ 260/243 C

[56] References Cited
UNITED STATES PATENTS

| | | | |
|---|---|---|---|
| 3,351,597 | 11/1967 | Higgins | 260/243 C |
| 3,516,997 | 6/1970 | Takano et al. | 260/243 C |
| 3,530,123 | 9/1970 | Takano et al. | 260/243 C |
| 3,563,983 | 2/1971 | Atarashi et al. | 260/243 C |
| 3,651,050 | 3/1972 | Nakanashi | 260/243 C |
| 3,739,002 | 6/1973 | Hayes et al. | 260/243 C |

*Primary Examiner*—Nicholas S. Rizzo
*Attorney, Agent, or Firm*—William C. Martens, Jr.; Everet F. Smith

[57] ABSTRACT

A 7-aminocephalosporin is acylated to a 7-acylamidocephalosporin by reaction with the pentachlorophenyl ester of sydnone-3-acetic acid or 1-tetrazoleacetic acid.

11 Claims, No Drawings

PROCESS FOR ACYLATING A 7-AMINOCEPHALOSPORIN

BACKGROUND OF THE INVENTION

Certain 7-sydnoneacylamido cephalosporins possessing antibacterial activity have been described and claimed in U.S. Pat. Nos. 3,530,123 and 3,563,983. Additionally, certain 7-tetrazolyacylamido cephalosporins have been described and claimed in U.S. Pat. No. 3,516,997.

In producing the compounds described in the above patents, a 7-aminocephalosporin can be acylated with an appropriate acylating agent so as to obtain the corresponding 7-acylamido cephalosporin derivative. Acylation of the 7-amino group of the cephalosporin to produce the 7-sydnoneacylamido cephalosporin has been accomplished in the above U.S. patents by reacting it will free acid derivative of the appropriate acyl group in the presence of a scavenger for the water which is formed as by-product. Such a scavenger can be, for example, N,N'-dicyclohexylcarbodiimide.

Also, in Naito et al., *The Journal of Antibiotics*, 21, pages 300–305 (1968), 7-aminocephalosporins were acylated to the corresponding 7-sydnoneacylamido derivatives using sydnone-3-acetyl chloride.

Additionally, U.S. Pat. No. 3,516,997 describes the acylation of a 7-aminocephalosporin by treatment thereof with a mixed anhydride produced from the acid of the selected acyl group and pivaloyl chloride.

The extent of success of the acylation is dependent upon the particular method which is employed as well as upon the structural characteristics of the particular acyl function which is to be attached to the 7-amino group of the cephalosporin.

It has now been discovered that it is possible to achieve a facile and highly successful acylation of the 7-amino group of a 7-aminocephalosporin to produce the corresponding 7-(sydnone-3-acetamido)- or 7-(1-tetrazoleacetamido)- derivative. This acylation involves the use as acylating agent of a specific ester of sydnone-3-acetic acid or 1-tetrazoleacetic acid.

SUMMARY OF THE INVENTION

This invention is directed to a process for acylating a 7-aminocephalosporin which comprises reacting said 7-aminocephalosporin or a silylated derivative thereof with a pentachlorophenyl ester of the formula

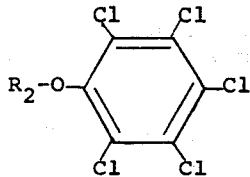

in which $R_2$ is a sydnone-3-acetyl or 1-tetrazoleacetyl.

Another aspect of this invention is the compound pentachlorophenyl 1-tetrazoleacetate. This compound is useful as acylating agent in the process of this invention.

DETAILED DESCRIPTION OF THE INVENTION

As already noted, this invention is directed to the use of particular esters in the process of acylating 7-aminocephalosporins. These esters have been found to be highly efficient in achieving acylation of 7-aminocephalosporins. The particular esters which are employed in the process of this invention are pentachlorophenyl sydnone-3-acetate and pentachlorophenyl 1-tetrazoleacetate. The extraordinary level of activity of the aforementioned esters has been found to arise from the combination of the pentachlorophenyl moiety and the particular characteristics of both the sydnone-3-acetic acid and 1-tetrazoleacetic acid moieties.

Multiple routes are available in preparing the esters which are employed in the process of this invention. For example, sydnone-3-acetic acid or 1-tetrazoleacetic acid itself can be reacted with pentachlorophenol. The reaction will generally be carried out in the presence of an appropriate water-scavenging condensing agent, such as, for example, N,N'-diethylcarbodiimide, N,N'-diisopropylcarbodiimide, N,N'-dicyclohexylcarbodiimide, and the like.

This ester formation can be carried out in the presence of any of a number of solvents, preferably polar solvents, such as N,N-dimethylformamide, N,N-dimethylacetamide, tetrahydrofuran, ethyl acetate, acetone, methyl ethyl ketone, acetonitrile, and the like. The ester formation generally will be carried out at a temperature of from about 0°C. to about 50°C. for a period of from about 1 to about 8 hours.

The esters used in the process of this invention also can be prepared by reacting sydnone-3-acetic acid or 1-tetrazoleacetic acid with an appropriate haloformate of pentachlorophenol. A haloformate which is highly suitable for this purpose is pentachlorophenyl chloroformate. This is obtained by reacting pentachlorophenol with phosgene. The thereby-obtained pentachlorophenyl chloroformate is then reacted with sydnone-3-acetic acid or 1-tetrazoleacetic acid to produce pentachlorophenyl sydnone-3-acetate or pentachlorophenyl 1-tetrazoleacetate, respectively. The reaction of pentachlorophenyl chloroformate with the acid may be carried out in a solvent, preferably a polar solvent, such as any of those previously mentioned. The temperature of reaction generally will range from about 0°C. to about 50°C., and the reaction will be carried out for from about 1 to about 8 hours.

Another method suitable for obtaining the esters used in the process of this invention includes the reaction of the appropriate acid halide, for example, sydnone-3-acetyl chloride or 1-tetrazoleacetyl chloride, with pentachlorophenol. The acid chloride can be obtained by treatment of the corresponding acid with phosphorus pentachloride. The acid chloride is treated with pentachlorophenol in the presence of a reagent which will scavenge the HCl byproduct, typically a tertiary amine, such as pyridine, triethylamine, and the like. The reaction generally is accomplished in the presence of an inert solvent such as any of those mentioned hereinabove.

In accordance with the process of this invention, the pentachlorophenyl esters are employed to acylate the 7-amino substituent present in a 7-amino cephalosporin. With respect to the structure of the 7-aminocephalosporin, the only critical element thereof is the presence of a free 7-amino substituent. Other substituents which appear in the molecule, especially in the 3- and/or 4-positions are not critical to the definition of the process of this invention. However, certain 7-aminocephalosporins are preferred for use in the process of this invention. Preferably, the 7-aminocephalosporin will have the formula

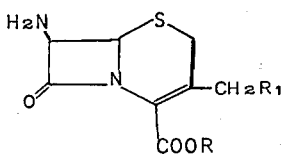

in which R is hydrogen, a carboxy protecting group, an amine salt cation, or an alkali or alkaline earth metal salt cation, and $R_1$ is hydrogen, acetoxy, methoxy, methylthio 5-methyl-1,3,4-thiadiazol-2-ylthio, 1-methyl-1H-tetrazol-5-ylthio, and the like.

Particularly preferred 7-aminocephalosporins which can be acylated in accordance with the process of this invention include those in which $R_1$ is hydrogen, acetoxy, 5-methyl-1,3,4-thiadiazol-2-ylthio, and 1-methyl-1H-tetrazol-5-ylthio.

The 7-aminocephalosporin can be used in the form of its free acid, in which case R is hydrogen. R can also be a carboxy protecting group, in which case the 7-aminocephalosporin typically will be in the form of an ester. The 7-aminocephalosporin can also be in the form of an amine salt, or an alkali or an alkaline earth metal salt. When the carboxy protecting group is an ester function, the particular structure of the ester function which is present on the 4-carboxyl group is not critical to the process of this invention. However, for ease of conversion to an active antibiotic, the ester function preferably should be one which is readily removable from the carboxyl substituent by recognized techniques. Preferably, therefore, in the event that an ester is employed, the R group defined in the above formula will be, for example, t-butyl, p-nitrobenzyl, p-methoxybenzyl, benzyl, benzhydryl, 2,2,2-trichloroethyl, or the like. Cleavage of the ester function to obtain an active antibiotic generally can be achieved by treatment of the ester with an acid such as trifluoroacetic acid, hydrochloric acid, and the like, or with zinc and acid, such as formic acid, acetic acid, or hydrochloric acid. Cleavage likewise can be accomplished by hydrogenating the ester in the presence of palladium, rhodium, or a compound thereof, in suspension or on a carrier such as barium sulfate, carbon, alumina, or the like.

The carboxy protecting group likewise can be a silyl ester group. Preferred such silyl groups include, for example, trimethylsilyl, triethylsilyl, tripropylsilyl, triphenylsilyl, and the like. More preferably, the silyl group is trimethylsilyl. Silylating agents suitable for achieving silyl ester formation include, for example, N,O-bis-(trimethylsilyl)acetamide, N-trimethylsilylacetamide, hexamethyldisilazane, and the like, as well as silylating agents containing other tri-substituted silyl moieties.

In those instances in which it is preferred to employ a carboxy protecting group, use of a silyl ester is highly preferred. The silyl ester is readily prepared from the corresponding free acid 7-aminocephalosporin, and, indeed, it can be prepared in situ during reaction of the 7-aminocephalosporin with the pentachlorophenyl ester. The silyl ester is prepared by reaction of the free acid 7-aminocephalosporin with an appropriate silylating agent, such as any of those mentioned hereinabove. Two silyl moieties are required for each 7-aminocephalosporin molecule; one silyl moiety attaches to the 4-carboxyl group and the other silyl moiety displaces one of the hydrogens at the 7-amino substituent. In the event, therefore, of the use of an in situ formed silyl ester, the pentachlorophenyl ester effectively will be reacted with a 7-aminocephalosporin in which one of the amine hydrogens has been displaced by a silyl moiety.

Cleavage of the silyl group from the 4-carboxyl function is accomplished during recovery of the acylated product, and, therefore, a specific cleavage step is not required. This is due to the fact that the silyl ester is quite labile and will be removed by simple hydrolysis under conditions employed during recovery of the 7-acylamidocephalosporin.

An amine salt, such as the dicyclohexylamine salt or the triethylamine salt of the 7-aminocephalosporin likewise can be used as reactant in the acylation. Moreover, an alkali or an alkaline earth metal salt such as the sodium, potassium, lithium, calcium, or the like, salt of the 7-aminocephalosporin can be employed.

In carrying out the acylation in accordance with the process of this invention, the selected 7-aminocephalosporin generally is dissolved in an appropriate solvent. If the 7-aminocephalosporin is employed in the form of its ester, such ester can be dissolved as such in the solvent or, in the case, for example, of a silyl ester, the silyl ester can be formed in situ by interaction of the free acid and a silylating agent. The pentachlorophenyl ester of sydnone-3-acetic acid or 1-tetrazoleacetic acid generally is then added to the mixture, and the reaction is allowed to proceed. Typically, the temperature of reaction is from about 0°C. to about 50°C., and preferably from about room temperature to about 40°C. The reaction is allowed to proceed to completion, which generally takes from about 1 to about 24 hours. The solvents which can be employed in the process of this invention generally are any solvents which accomplish dissolution of both the 7-aminocephalosporin and the pentachlorophenyl ester. Generally, therefore, a solvent which is moderately polar is employed, and, thus, includes solvents such as tetrahydrofuran, acetonitrile, N,N-dimethylformamide, N,N-dimethylacetamide, acetone, methyl ethyl ketone, ethyl acetate, and the like. The amount of solvent which is employed is not critical to the process of this invention. An amount of solvent sufficient to accomplish complete dissolution of the reactants generally will be employed.

The reaction is equimolar, and typically therefore equivalent quantities of the reactants are employed. However, it, of course, is preferred to employ a slight excess of the less expensive reactant to assure maximum conversion of the more expensive reactant. Thus, an excess of from about 5 percent to about 15 percent on a molar basis of the pentachlorophenyl ester generally is employed.

The product from the process of this invention can be recovered as the free acid, as the alkali or alkaline earth metal salt, such as the sodium, potassium, or calcium salt, as an ester, or as an acid addition salt, such as, for example, the dicyclohexylamine salt, the triethylamine, salt, the quinoline salt, and the like.

The products produced in accordance with the process of this invention can be isolated by employing conventional methods. These can include, for example, chromatographic separation, filtration, recrystallization, and the like.

Compounds which can be prepared in accordance with the process of this invention include, but by no means are limited to, the following: 7-(syndone-3-acetamido)-3-methyl-3-cephem-4-carboxylic acid; t- butyl 7-(sydnone-3-acetamido)-3-acetoxymethyl-3-cephem-4-carboxylate; p-nitrobenzyl 7-(1-tetrazoleacetamido)-3-acetoxymethyl-3-cephem-4-carboxylate; p-methoxybenzyl 7-(1-tetrazoleacetamido)-3-(5-methyl-1,3,4-thiadiazol-2-ylthiomethyl)-3-cephem-4-carboxylate; benzyl 7-(sydnone-3-acetamido)-3-(5-methyl-1,3,4-thiadiazol-2-ylthiomethyl)-3-cephem-4-carboxylate; benzhydryl 7-(sydnone-3-acetamido)-3-(1-methyl-1H-tetrazol-5-ylthiomethyl)-3-cephem-4-carboxylate; 2,2,2-trichloroethyl 7-(1-tetrazoleacetamido)-3-methylthiomethyl-3-cephem-4-carboxylate; 7-(sydnone-3-acetamido)-3-acetoxymethyl-3-cephem-4-carboxylate; 7-(1-tetrazoleacetamido)-3-acetoxymethyl-3-cephem-4-carboxylic acid; 7-(sydnone-3-acetamido)-3-(5-methyl-1,3,4-thiadiazol-2-ylthiomethyl)-3-cephem-4-carboxylic acid; 7-(1-tetrazoleacetamido)-3-(5-methyl-1,3,4-thiadiazol-2-ylthiomethyl)-3-cephem-4-carboxylic acid; and the like.

The following examples are provided to further illustrate the teaching of this invention, and are not intended to be limiting upon the scope thereof.

EXAMPLE 1

Preparation of pentachlorophenyl sydnone-3-acetate.

Employing the procedure described in *Chemical Abstracts*, 55, 103906 (1961), pentachlorophenyl chloroformate was prepared as follows:

About 27 g. (0.1 mole) of pentachlorophenol were added to about 100 ml. of water followed by about 8 g. (5.3 ml.) of 50 percent aqueous sodium hydroxide. The pH of the resulting mixture was about pH 9, and most of the pentachlorophenol had gone into solution. The resulting mixture was diluted to a total volume of about 180 ml. by addition of water. A solution of about 10 ml. of phosgene dissolved in 40 ml. of benzene was added dropwise while the reaction mixture was maintained at a temperature of about 8°–10°C. with cooling. During the dropwise addition, 20 percent aqueous sodium hydroxide was added as necessary to maintain the pH of the mixture above about pH 7. The lower benzene layer was separated from the aqueous layer, additional benzene was added, and the benzene was washed with cold water. The benzene layer was then dried over magnesium sulfate and evaporated to produce a crystalline residue of 29.5 g. of pentachlorophenyl chloroformate, m.p. 54°–61°C.

About 3.2 ml. (40 millimoles) of pyridine were added to 5.76 g. (40 millimoles) of sydnone-3-acetic acid dissolved in 50 ml. of tetrahydrofuran. To the slurry of the resulting pyridine salt were added 13.2 g. (40 millimoles) of the above prepared chloroformate dissolved in 50 ml. of tetrahydrofuran. The mixture was stirred for about one hour during which time carbon dioxide evolved and was vented from the system. The reaction mixture was then filtered, and the filtrate was evaporated. The resulting residue was slurried with ether, filtered and dried in vacuo to give 14.1 g. of product comprising the pentachlorophenyl sydnone-3-acetate. The solid was further purified by slurrying in water, washing with ether, and drying in vacuo to recover pentachlorophenyl sydnone-3-acetate, m.p. 188°–91°C.

Analysis, Calculated for $C_{10}H_3N_4O_6Cl_5$: C, 30.61; H, 0.77; N, 7.14. Found: C, 30.83; H, 0.76; N, 7.04.

EXAMPLE 2

Preparation of 7-(sydnone-3-acetamido)-3-(5-methyl-1,3,4-thiadiazol-2-ylthiomethyl)-3-cephem-4-carboxylic acid.

To about 50 ml. of dry acetonitrile were added 2.75 g. (8 millimoles) of 7-amino-3-(5-methyl-1,3,4-thiadiazol-2-ylthiomethyl)-3-cephem-4-carboxylic acid. About 5 ml. of N,O-bis(trimethylsilyl)acetamide were added to the mixture, and the mixture was warmed to about 50°C. The suspension of solids dissolved after about 15 minutes. The reaction mixture, maintained in a nitrogen atmosphere, was allowed to cool to room temperature. About 4.7 g. (12 millimoles) of pentachlorophenyl sydnone-3-acetate were added. The mixture was stirred for about 2 hours, after which time undissolved solids remained in the mixture. The mixture was then stirred overnight with the result that all solids dissolved. About 1.5 ml. of methanol were added, and 0.15 g. of a solid precipitated which was removed by filtration. About 5 ml. of water were then added to the filtrate followed by the dropwise addition of 1.5 ml. of dicyclohexylamine. Crystallization occurred, and the mixture was stirred at room temperature for about 2 hours. The solid was collected by filtration, washed with a solution of 90 percent acetonitrile and 10 percent water, and dried in vacuo. About 3.5 g. (67 percent yield) of the dicyclohexylamine salt of 7-(sydnone-3-acetamido)-3-(5-methyl-1,3,4-thiadiazol-2-ylthiomethyl)-3-cephem-4-carboxylic acid, m.p., 169°–74°C., were thereby obtained. Thin-layer chromatography of this material produced only one spot.

The above dicyclohexylamine salt was stirred in 28 ml. of ethanol. About 2.5 ml. of water were added, followed by the dropwise addition of a mixture prepared by adding 3.1 ml. of a 70 percent aqueous sodium lactate solution to 7 ml. of ethanol. The mixture was stirred for about 4 hours, and the precipitated product was collected by filtration, washed with ethanol, and dried in vacuo at about 40°C. About 2.3 g. (58 percent yield) of the sodium salt of 7-(sydnone-3-acetamido)-3-(5-methyl-1,3,4-thiadiazol-2-ylthiomethyl)-3-cephem-4-carboxylic acid, were thereby obtained.

EXAMPLE 3

Preparation of 7-(sydnone-3-acetamido)-3-(5-methyl-1,3,4-thiadiazol-2-ylthiomethyl)-3-cephem-4-carboxylic acid.

To about 25 ml. of dry N,N-dimethylformamide were added 2.75 g. (8 millimoles) of 7-amino-3-(5-methyl-1,3,4-thiadiazol-2-ylthiomethyl)-3-cephem-4-carboxylic acid. About 5 ml. of N,O-bis(trimethylsilyl)acetamide were added at room temperature. The reaction mixture immediately became a clear solution. About 4.7 g. (12 millimoles) of pentachlorophenyl sydnone-3-acetate were added to the reaction mixture. The mixture was stirred overnight. About 1.5 ml. of methanol were then added to the mixture; however, no precipitate formed. The solution was then evaporated at about 60°C. to a dark oil; however, the oil did not crystallize upon addition either of ether or of ethyl acetate. The mixture was again concentrated, and about 50 ml. of acetonitrile were added. The resulting solution was filtered, and about 1.5 ml. of dicyclohexylamine were added to the filtrate. Crystals of the dicyclohexylamine salt precipitated rapidly. The mixture was stirred for about two hours, and the solid was collected, washed with acetonitrile, and dried in vacuo. The solid product was then slurried in about 20 ml. of ethanol for about 30 minutes, filtered, washed with ethanol and dried. The dicyclohexylamine salt of 7-

(sydnone-3-acetamido)-3-(1,3,4-thiadiazol-2-ylthiomethyl)-3-cephem-4-carboxylic acid, in an amount of 4.33 g. (83 percent yield), was collected.

Analysis, Calculated for $C_{27}H_{35}N_7O_6S_3$C, 49.75; H, 5.72; N. 15.04. Found: C, 49.69; H, 5.48; N, 14.77.

In accordance with the method of Example 2, the dicyclohexylamine salt was converted to 2.76 g. (70 percent yield) of the corresponding sodium salt.

EXAMPLE 4

Preparation of 7-(sydnone-3-acetamido)-3-(5-methyl-1,3,4-thiadiazol-2-ylthiomethyl)-3-cephem-4-carboxylic acid.

To about 50 ml. of tetrahydrofuran were added 2.75 g. (8 millimoles) of 7-amino-3-(5-methyl-1,3,4-thiadiazol-2-ylthiomethyl)-3-cephem-4-carboxylic acid followed by about 5 ml. of N,O-bis(trimethylsilyl)acetamide. The mixture was heated to reflux, and the contents quickly dissolved. The resulting solution was then blanketed with nitrogen and allowed to cool. At about 40°C., 4.70 g. (12 millimoles) of pentachlorophenyl sydnone-3-acetate were addded. When the added pentachlorophenyl ester had dissolved, nitrogen addition was halted, and the reaction flask was sealed. The mixture was stirred overnight.

To the resulting stirred solution were added 2 ml. of methanol. No noticeable precipitation occurred. The reaction mixture was then stirred with two portions of saturated aqueous sodium chloride to which had been added sufficient 6N HCl to lower the pH to about 1. The organic layer was separated from the aqueous layer, dried over magnesium sulfate, and evaporated to dryness. A solid residue resulted which was triturated in ether, collected by filtration, and dried in vacuo. The residue then was stirred in a mixture of water and ethyl acetate, and 1N aqueous sodium hydroxide was added to raise the pH of the aqueous layer to about 7. The aqueous layer was then separated from the organic layer, and the aqueous layer was extracted two times with ethyl acetate. The aqueous layer was then overlayed with acetonitrile, and 6N HCl was added to lower the pH to about 2. A small amount of sodium chloride was then added. The acetonitrile layer was separated and was shaken with saturated aqueous sodium chloride. The acetonitrile layer was then dried over magnesium sulfate and evaporated to produce a solid residue. The solid residue was slurried in ether and filtered to obtain 2.85 g. of 7-(sydnone-3-acetamido)-3-(5-methyl-1,3,4-thiadiazol-2-ylthiomethyl)-3-cephem-4-carboxylic acid.

EXAMPLE 5

Preparation of pentachlorophenyl 1-tetrazoleacetate.

To a solution of 2.7 g. (10 millimoles) of pentachlorophenol in 25 ml. of acetone were added 1.5 g. (10 millimoles) of 1-tetrazoleacetyl chloride. Pyridine (3 ml.) was added to the mixture. The mixture was stirred for 2 hours and then allowed to stir overnight. Water was added to the reaction mixture, and a precipitate formed. The solid precipitate was collected, washed successively with water and ether, and dried in vacuo to obtain 1.8 g. (48 percent per yield) of pentachlorophenyl 1-tetrazoleacetate, melting point 203°–205°C. (dec.).

Analysis, Calculated for $C_9H_3N_4O_2Cl_5$: C, 28.72; H, 0.80; N, 14.88; Cl, 47.09. Found: C, 27.65; H, 0.79; N, 13.93; Cl, 46.95.

EXAMPLE 6

Preparation of 7-(1-tetrazoleacetamido)-3-(5-methyl-1,3,4-thiadiazol-2-ylthiomethyl)-3-cephem-4-carboxylic acid.

A mixture of 2.75 g. (8 millimoles) of 7-amino-3-(5-methyl-1,3,4-thiadiazol-2-ylthiomethyl)-3-cephem-4-carboxylic acid and 3 g. of N-trimethylsilylacetamide in 15 ml. of N,N-dimethylformamide was prepared. The mixture was warmed to about 40°C. during which time solution was effected and then was cooled to about 30°C. To the solution was then added 3.3 g. (8.8 millimoles) of pentachlorophenyl 1-tetrazoleacetate. The mixture was stirred for about 2 hours after which it was diluted by addition of 1 ml. of methanol and 50 ml. of acetonitrile. The solution was decolorized with activated charcoal, and dicyclohexylamine (1.6 ml.) was added. A solid formed which, after 30 minutes, was collected, washed with acetonitrile and ethanol, and dried in vacuo to provide 3.65 g. (72 percent) of the dicyclohexylamine salt of 7-(1-tetrazoleacetamido)-3-(5-methyl-1,3,4-thiadiazol-2-ylthiomethyl)-3-cephem-4-carboxylic acid. The dicyclohexylamine salt was converted to the free acid, and an NMR spectrum of the free acid is consistent with the designated structure.

I claim:

1. A process for acylating a 7-aminocephalosporin which comprises the step of reacting said 7-aminocephalosporin or a silylated derivative thereof with a pentachlorophenyl ester of the formula

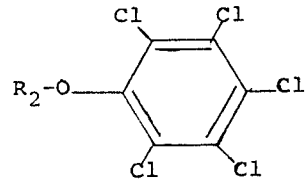

in which $R_2$ is sydnone-3-acetyl or 1-tetrazoleacetyl.

2. Process of claim 1, in which the 7-aminocephalosporin has the formula

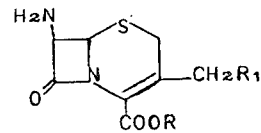

in which R is hydrogen, a carboxy protecting group, an amine salt cation, or an alkali or alkaline earth metal salt cation, and $R_1$ is hydrogen, acetoxy, methoxy, methylthio, 5-methyl-1,3,4-thiadiazol-2-ylthio, or 1-methyl-1H-tetrazol-5-ylthio.

3. Process of claim 2, in which R is a carboxy protecting group.

4. Process of claim 3, in which R is selected from the group consisting of t-butyl, p-nitrobenzyl, p-methoxybenzyl, benzyl, benzhydryl, and 2,2,2-trichloroethyl.

5. Process of claim 3, in which R is a silyl group.

6. Process of claim 5, in which R is trimethylsilyl.

7. Process of claim 6, in which $R_1$ is acetoxy.

8. Process of claim 6, in which $R_1$ is 5-methyl-1,3,4-thiadiazol-2-ylthio.

9. Process of claim 1, in which $R_2$ is sydnone-3-acetyl.

10. Process of claim 1, in which $R_2$ is 1-tetrazoleacetyl.

11. Process of claim 1, in which a free acid 7-aminocephalosporin is first reacted with a silylating agent, and the silylated derivative of said free acid 7-aminocephalosporin is then reacted with said penta- chlorophenyl ester.

* * * * *